United States Patent [19]

Sibalis et al.

[11] Patent Number: 5,591,123

[45] Date of Patent: Jan. 7, 1997

[54] PROGRAMMABLE CONTROL MOUNTING SYSTEM FOR TRANSDERMAL DRUG APPLICATOR

[75] Inventors: Dan Sibalis, Stony Brook; Sanford Rosen, New York, both of N.Y.

[73] Assignee: Drug Delivery Systems Inc., New York, N.Y.

[21] Appl. No.: 381,141

[22] Filed: Jan. 30, 1995

Related U.S. Application Data

[60] Continuation of Ser. No. 858,685, Mar. 27, 1992, abandoned, which is a division of Ser. No. 711,589, Jun. 6, 1991, Pat. No. 5,135,479, which is a continuation of Ser. No. 396,746, Jul. 18, 1989, abandoned, which is a continuation of Ser. No. 555, filed as PCT/US85/01075 Jun. 10, 1985, abandoned, which is a continuation-in-part of Ser. No. 839,050, Mar. 12, 1986, Pat. No. 4,640,689, which is a continuation of Ser. No. 702,486, filed as PCT/US85/00080 Jan. 17, 1985, abandoned, which is a continuation-in-part of Ser. No. 660,192, Oct. 12, 1984, Pat. No. 4,622,031, which is a continuation-in-part of Ser. No. 542,252, Aug. 18, 1983, Pat. No. 4,557,723.

[51] Int. Cl.$^6$ .................................................. A61N 1/30
[52] U.S. Cl. ........................... 604/20; 128/690; 607/149; 607/152
[58] Field of Search ................................ 604/20; 128/635, 128/666, 690; 607/149, 152

[56] References Cited

U.S. PATENT DOCUMENTS

| | | | |
|---|---|---|---|
| 3,991,755 | 11/1976 | Vernon et al. | 604/20 |
| 4,163,447 | 8/1979 | Orr | 128/666 |
| 4,259,963 | 4/1981 | Huch | 128/666 |
| 4,292,968 | 10/1981 | Ellis | 604/20 |
| 4,406,658 | 9/1983 | Lattin et al. | 128/419 R |
| 4,416,274 | 11/1983 | Jacobsen et al. | 604/20 |
| 4,460,368 | 7/1984 | Allison et al. | 604/896 |
| 4,494,950 | 1/1985 | Fischell | 128/635 |
| 4,577,723 | 12/1985 | Sibalis | 604/20 |
| 4,622,031 | 11/1986 | Sibalis | 604/20 |
| 4,640,689 | 2/1987 | Sibalis | 604/20 |
| 4,708,716 | 11/1987 | Sibalis | 604/20 |
| 4,725,263 | 2/1988 | McNichols | 604/20 |
| 4,931,046 | 6/1990 | Newman | 604/20 |
| 5,087,241 | 2/1992 | Mathiesen et al. | 128/803 |
| 5,135,479 | 8/1992 | Sibalis et al. | 128/802 |
| 5,163,899 | 11/1992 | Sibalis | 604/20 |
| 5,167,617 | 12/1992 | Sibalis | 128/798 |

OTHER PUBLICATIONS

Spencer, "Programmable Nanoampere Constant Current Sources for Iontophoresis", Med. & Biol. Engr. vol. 9, (1971), pp. 683–702.

*Primary Examiner*—Paul B. Prebilic
*Attorney, Agent, or Firm*—Lackenbach Siegel Marzullo Aronson & Greenspan, P.C.

[57] ABSTRACT

A transdermal drug applicator (100) for application to a living body for the delivery of at least one drug through the skin (144) into the bloodstream comprising an applicator (100) including at least one drug reservoir (182A, 182B) containing the drug for delivering same through the skin (144) by physico/chemical mass transfer. A mounting structure (138, 140) is removably mounted to the body for holding the applicator (100) to the skin (144), with the applicator (100) removably connected to the mounting structure (138, 140). A power supply (166) for the applicator (100) and a circuit transmitting electrical power from the power supply (166) to the applicator (100) is disclosed, wherein an electric circuit is created between the applicator (100) and the skin (144). The device includes a computer (158) with the mounting structure (138, 140) for receiving programmed instructions relative to the drug, and transmitting signals relative to the drug and the programmed instructions to the power supply (166) for regulating the generation of power and delivery of drug through the skin (144).

7 Claims, 8 Drawing Sheets

PROGRAMMABLE CONTROL MOUNTING SYSTEM FOR TRANSDERMAL DRUG APPLICATOR

This application is a continuation of Ser. No. 07/858,685, filed Mar. 27, 1992, now abandoned, which is a divisional of Ser. No. 711,589, filed Jun. 6, 1991, now U.S. Pat. No. 5,135,479, which is a continuation of Ser. No. 396,746, filed Jul. 18, 1989, now abandoned, which is a continuation of Ser. No. 000,555, filed Jan. 5, 1987, now abandoned (and based on PCT/US85/01075, filed Jun. 10, 1985), which is a continuation-in-part of Ser. No. 839,050, filed Mar. 12, 1986, now U.S. Pat. No. 4,640,689, which is a continuation of Ser. No. 702,486, filed Feb. 19, 1985, now abandoned, and originating from PCT/US85/00080, filed Jan. 17, 1985, which is a continuation-in-part of Ser. No. 660,192, filed Oct. 12, 1984, now U.S. Pat. No. 4,622,031, which is a continuation-in-part of Ser. No. 524,252, filed Aug. 18, 1983, now U.S. Pat. No. 4,557,723.

FIELD OF THE INVENTION

This invention relates to transdermal drug applicators, as well as to electrode constructions for use with such applicators; and more particularly to drug applicators which are mounted to a control system and is also mounted in operative relationship to the skin of an animal or a human being.

BACKGROUND OF THE INVENTION AND DISCUSSION OF THE PRIOR ART

The delivery of medicament through an animal's skin of an animal or of a person utilizing electrophoresis and/or electro-osmosis is one where the drug molecules in solution or suspension are made subject to an electric field, and in case of electrophoresis, if the electrode having the same charge as that of the ionic molecules is above the solution adjacent the skin which is the site of administration, the ions will be repelled and migrate through the skin into the blood stream; whereas in the case of electro-osmosis, a solution of water is attracted to the negative electrode, and thus any electric current flowing through a porous membrane causes a flow therethrough. Such electrochemical processes, although similar in end result do, however, function together, but separately or independently, in pumping and/or delivering a drug or other medication transdermally.

Transdermal drug applicators of the type being discussed herein are dependent upon application of electrical current to the electrical circuit including the drug reservoir(s) and the skin of the patient. Delivery of the drug to a patient, for example, is best accomplished at a steady state, at constant rate, often over a long period of time and/or on demand. Beneficial results of the drug transfer are lessened if the patient forgets at times to activate the drug delivery mechanism, so that delivery of the drug often takes place at the hospital. If the patient operates the delivery mechanism, delivery can be expected to be irregular.

It is therefor a principal object of this invention to provide a system that both mounts the drug applicator to the skin of a patient and that automatically times the activation and deactivation of an electrical power supply of the system to accomplish delivery and cessation of delivery of a drug by electrophoretic and/or electro-osmotic deposition at a variable controlled rate at preset or preprogrammed time intervals.

It is another object of this invention to provide a system that secures a drug reservoir or reservoirs to the skin of a patient and that includes a computer mechanism that can be programmed to signal the activation and deactivation of a power supply mounted in the system for delivery and cessation of delivery of a drug or drugs by electrophoretic and/or electro-osmotic deposition at a controlled rate at preset time intervals.

It is another object of the invention to provide a system which responds for controlling delivery of a drug to a patient that includes a response to physical and chemical changes experienced by the subject or patient, by providing a closed loop feedback system or in effect providing an on demand drug delivery system.

Other objects and advantages of this invention will hereafter become obvious from the following description of the preferred embodiments of this invention.

Reference to or disclosure of devices for transdermal delivery of drugs by application of electrical current through the skin of a person or animal are shown in the following U.S. Pat. Nos.:

| | |
|---|---|
| 385,556 | 4,243,052 |
| 486,902 | 4,325,367 |
| 588,479 | 4,367,745 |
| 2,493,155 | 4,419,091 |
| 2,267,162 | 4,474,570 |
| 2,784,715 | 4,406,658 |
| 3,163,166 | 4,314,554 |
| 3,289,671 | 4,166,457 |
| 3,547,107 | 4,239,052 |
| 3,677,268 | 4,290,878 |
| 4,008,721 | 4,164,226 |
| 4,141,359 | 4,362,645 |
| 4,239,046 | 4,273,135 |

The following foreign patents refer to or disclose transdermal delivery devices:

EPA 0060452

DE 290202183

DE 3225748

EPA 0058920

UK 2104388

SUMMARY OF THE INVENTION

In accordance with the above objects and with other objects that will become apparent in the course of this application, there is provided herein a transdermal drug applicator for application to a living body for the delivery of at least one drug through the skin and the like into the blood stream comprising: applicator means including at least one drug reservoir containing said drug for delivering said drug through said skin by a physico/chemical mass transfer of said drug; mounting means removably mounted to said body for holding said applicator means being removably connected to said mounting means; power means for and associated with said applicator means; circuit means for transmitting electrical power received from said power means to said applicator means wherein an electric circuit is created between said applicator means through said skin; and computer means associated with said mounting means for receiving programmed instructions relative to said drug, and for transmitting signals relative to said drug and said programmed instructions to said power means for regulating the generation of power and delivery of said drug through said skin.

Also, the invention relates to an electrokinetic transdermal drug applicator adapted to be adhered to the said skin and the drug reservoir for controlling and maintaining drug delivery for a predetermined time, comprising: drug reservoirs having at least one drug and having a plurality of electrodes and a power source for providing the mass transfer of said drug through the skin of said subject by means of electrokinetic phenomena; and at least one buffering means associated with at least one of said drug reservoirs and the interface between said skin and said drug reservoirs; said at least one buffering means being capable of maintaining a pH for an optimum rate of drug delivery.

In addition, an electrokinetic transdermal drug applicator adapted to be adhered to the skin of a subject at an interface between said skin and the drug reservoir for maintaining the pH range of said skin at said interface comprising drug reservoirs having at least one drug and having a plurality of electrodes and a power source for providing the mass transfer of said drug through the skin of said subject by means of electrokinetic phenomena; and at least one buffering means at said skin interface for limiting the pH changes at said skin interface within a range which is non-irritating to the subject's skin,

DESCRIPTION OF THE PREFERRED EMBODIMENTS

Figure 1:
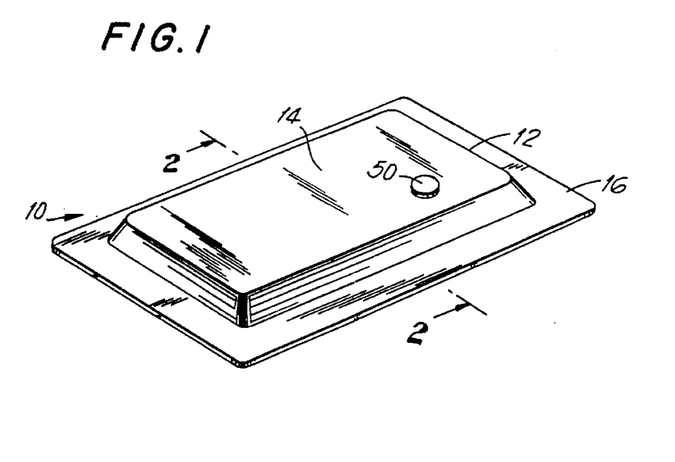
FIG. 1 is an isometric view of an applicator embodying the principles of this invention.
Figure 2:
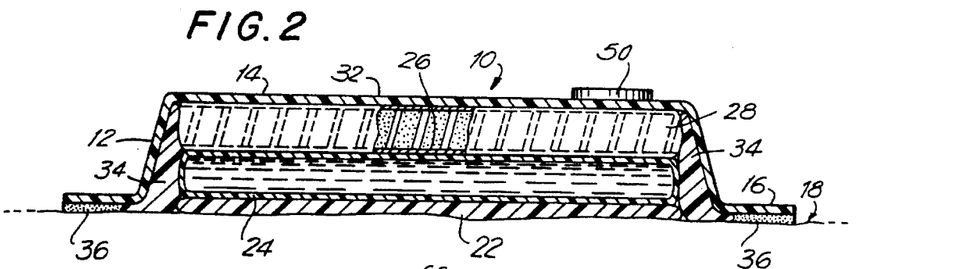
FIG. 2 is a cross-sectional view taken along the line 2—2 of FIG. 1 showing the applicator mounted on the skin.

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electro-phoresis and/or electroosmosis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semi-permeable membrane 22 through which the medicament migrates to be delivered through the skin 18. As will be noted from the following discussion, membrane 22 may not be needed, depending on the nature of the reservoir for the medicament.

The second layer consists of a flexible pad or other type reservoir 24 containing the drug to be administered. As is understood in the art, and shown in one or more of the U.S. patents identified above, reservoir 24 can be an impregnated pad or a gel containing the drug of choice in solution or suspension, the walls of which are sufficiently dense to prevent leakage of the drug under ambient conditions, but sufficiently porous to permit migration of the drug, such as, for example, the charged particles or ions under the influence of the electric field imposed when utilizing electrophoresis. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure on the nature of the medicament involved. In the alternative, reservoir 24 can consist of porous material in which the drug is impregnated rather than a pouch Containing the liquid medicament.

The third or next layer above reservoir 24 is an extended contact 26 which could be incorporated as one face of battery 28 which is the next layer. Contact 26 could be any suitable conductive material, preferably body-conformable, to permit applicator 10 so as to..be curved or bent to conform to the shaped surface of the skin. Suitable materials of this type are well known in the art and include electrically conductive polymers, preferably non-ionic. Carbon loaded or surface metalized plastics are also available for such use.

Battery 28 comprising the next layer can be made up of a group of cells internally connected in series to obtain the desired voltage necessary to obtain the electro-kinetic action with the particular medicament, and orientation of battery 28 would depend on whether the charged particles of the drug of choice are positive or negative. If the particles are negatively charged in solution or suspension, then contact 26 would be connected to the negative side of battery 28 as the skin will then be positive with respect to that contact and will attract the ions. With electro-osmosis, greater flexibility in design and structure is permissible as, for example, the pH of the drug solution is not as important. Moreover, the solution can be highly concentrated which is in contrast to that of an ionic solution, which requires high ion mobility and thus lower concentrations. Consequently, although both types of drug delivery systems are contemplated herein and come within the scope of this invention, the sytem utilized should be based upon drug chosen. Both systems are combinable or can be used simultaneously to maximize the efficiency of the product or to make it possible to deliver non-ionic drugs and/or large rates of delivery.

With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11 and 24. When such a battery is employed, sheets may be layered to place the cells in series in a diagonal as shown somewhat schematically in FIG. 2. Of course, battery selection would ultimately depend on such factors as the degree of conformability desired, voltage and current densities required for a specific application, and time of discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as polymer impregnated with carbon or surface metalized plastic. Insulating material 34 fills the space between the side wall of raised portion 14 and the various layers contained therein.

An electrically conductive adhesive material 36 coats the underside of lip 16 so that applicator or device 10 may be placed on and adhere to skin 18 and make good electrical contact.

It will be seen that the above described arrangement in general forms a complete electric circuit from one side of battery 28, cover 12, adhesive material 36, skin 18, microporous membrane 22, liquid reservoir 24, and back to battery 28.

Figure 3:
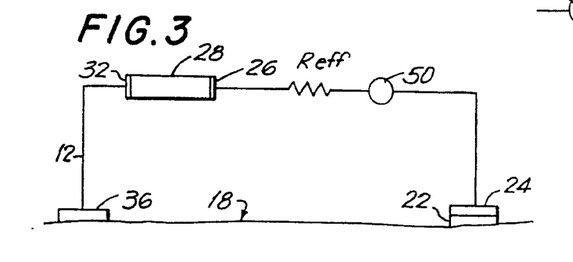
FIG. 3 is a schematic of electrical circuitry incorporated in the embodiment shown in FIGS. 1 and 2 showing an LCD indicator.

For a more particular description of the electrical circuit formed by the arrangement just described, reference is made to FIG. 3 wherein the circuit is shown schematically with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22. In a system of this type, one of the aims is to establish a very low specific rate of current flow so that the medicament will be deposited slowly over a long period of time. Current flow of down as low as 0.0001 ampere per square centimeter of skin surface below membrane 22 is a typical current which may be selected for the application of a particular drug. Electrical resistance of the skin to current flow is of the order of 6–9K ohms and is roughly independent of the distance between the points on the skin where electrical contact is made. This is because skin electrical resistance is largely that of resistance to penetration, the current flowing through the fluids of the body in which electrical resistance is very low. Thus, in order to establish current flow at the rate indicated, by Ohm's law, it is seen that total resistance of the circuit using a 1.5 volt battery should be about 360K ohms for each square centimeter of application. This resistance, the effective resistance, Reff, of the circuit, can be built into any one component or combination of components of the circuit shown in FIG. 3, including the battery resistance, electrodes, cover material, etc. In addition, if desired, in order to maintain current flow constant over the full period of operation, a constant current limiting device can be made integral with and a part of conductor 26, or any other part of the circuit where it is found convenient to do so.

Figure 4:
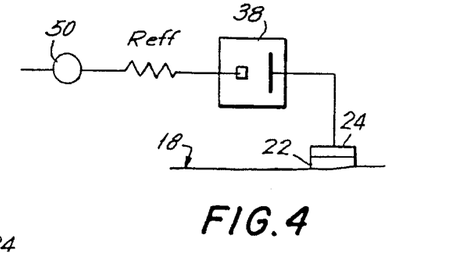
FIG. 4 is an alternative embodiment for the circuit shown in FIG. 3.

Furthermore, as indicated schematically in FIG. 4, applicator 10 may be designed to incorporate a provision to insure that the deposit of medicament will cease after a given period of time or after a certain quantity of drug is administered. This can be accomplished by employing a programable integrator circuit or by inserting in the circuit an integrating device such as a reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delviered, there is a large increase in internal resistance resulting in a substantial drop of current flow and an effective halt to drug migration. Such a device can be employed to establish in advance the period of time over which the medicament is to be applied or, as noted above, the quantity of the drug to be delivered. Cell 38 is a relatively high resistance device and could provide for much of the high resistance requried for the operation of applicator 10.

Cell 38 may be made a part of contact 32 or be inserted between contact 32 and cover material 14. In addition, provision may be made for current flow to be built up gradually to avoid any feelings or sensations to the recipient of the drug.

In FIGS. 1–4, there is shown liquid crystal display (LCD) 50 which is incorporated in the structure and circuitry of device 10. LCD 50 is designed so that it will cause a change in the light appearance only at and with the constant prescribed current of device 10. That is, with a completed circuit at such constant current, the prescribed dosage of medicament is being transcutaneously administered to the user, and LCD is light indicating so as to give a positive indication of this drug administration. In the event of (1) a broken circuit, such as a loosening of the conductive lip from the skin surface, (2) a dissipated or faulty battery, or (3) depletion of the medicament, so as to cause a failure of the constant current, the LCD will now show the liquid crystal display change, and the user will be informed that the prescribed drug is not being administered. The user is thus given a clear positive indication that either the drug is being properly administered or the drug is not being properly administered. In the latter event, the user merely removes the device and applies a new device, and upon the new application, the new LCD will be activated.

While the invention has hereinabove been described in the context of an LCD, light emitting diodes (LED) are also within the contemplation of this invention.

With the presence of indicator 50, the complete circuit is formed by skin 18, adhesive layer 36, cover 12, battery 28, indicator 50, contacts 32 and 26, filled reservoir 24, member 22 and resistor Reff.

As will be hereinafter discussed in greater detail, the use of a programable computer display, either digital or analog, may be employed to show the status of the regiment of drug delivery and in case of malfunction, such as loss of skin contact or a weak battery, the device would give an audible or mechanical (vibration) alert to the patient. Such a programmable computer device is particularly applicable in drug applicators as exemplified in those applicators shown in FIGS. 12–21.

Figure 5:
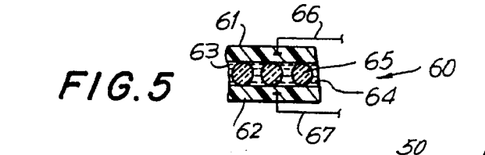
FIG. 5 is an enlarged sectional view of an alternative indicator embodiment.

Referring now to FIG. 5, there is shown a greatly enlarged sectional view of an alternate embodiment 60 for indicator 50. Indicator 60 comprises electroconductive polymeric upper and lower layers 61 and 62, respectively. Layers 61 and 62, in conjunction with non-conductive polymeric end caps (not shown), form a reservoir 63. Upper layer 61 has at least one transparent portion or is fully transparent for purposes hereinafter appearing. An electro-chemically conductive phototropic material in the form of a solution or gel 64 is disposed in reservoir 63. A uni-layer of silica particulates 65 disposed in reservoir 63 so as to provide non-conductive spacing for layers 61 and 63.

Electrical leads 66 and 67 are provided to complete the circuit with battery 28 and contact 24, respectively.

Electrochemically phototropic or electrochromic materials will change color or appearance with the passage of the current through the material. Reservoir 63 is filled with such color changing material which is viewable by the user through transparent upper layer 61 of the present device. Suitable electrochemical phototropic materials include, by way of example, those ion change sensitive indicator dyes as disclosed in U.S. Pat. No. 4,013,414, granted Mar. 22, 1977 to Lavalee et al. By providing a highly polar condition in the indicator of the present invention, such ion change sensitive indicator dye color variations would be detected, thereby informing the patient that the medicament is being administered.

It is also within the contemplation of the present invention that the device's constant current be utilized to effect a change in electromotive force, or other kinetic energy on a chemical and/or dye material which is color-responsive or phototropic with such change, so as to serve as an indicator. Such suitable dye materials are, by way of example, disclosed in U.S. Pat. No. 4,362,645, granted Dec. 7, 1982 to Hof et al.

Applicator 10 may be prepared in advance in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired, such as behind the ear, or in contact with any mucous membrane.

Current flow rate starts immediately along with migration of the drug.

The use of the invention as herein described makes it possible for the first time to provide for drug therapy over an extended period of time with a degree of control and accuracy which heretofore has not been possible or practical. The cost of such therapy using this invention is reduced significantly with the result that extensive use of the invention will have a favorable economic impact on medical care. The indicator now provides a positive degree of assurance to the user not heretofore available in body worn medicament dispensers.

Figure 6:
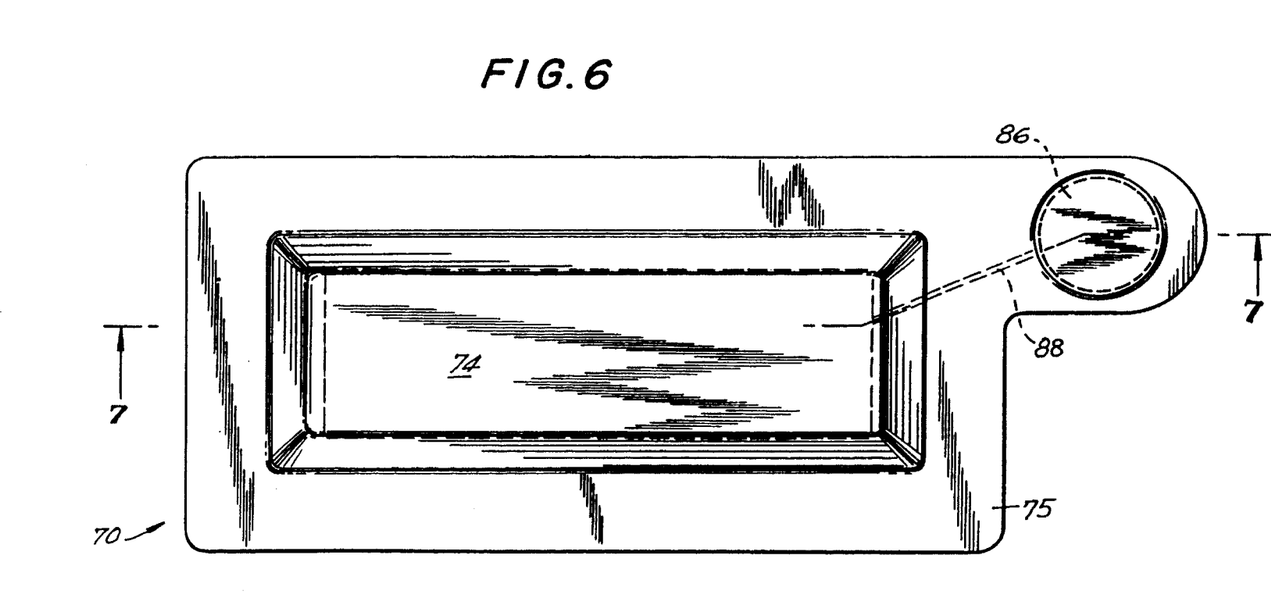
FIG. 6 is a plan view of an alternative applicator similar to that of FIGS. 1 and 2 further incorporating a third or feedback electrode.
Figure 7:
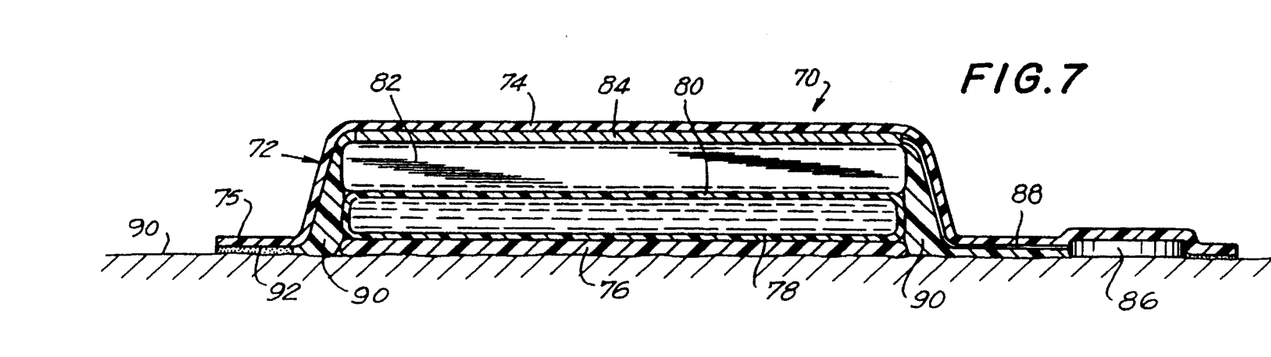
FIG. 7 is a sectional view taken along the line 7—7 of FIG. 6 showing the applicator mounted on the skin.
Figure 8:
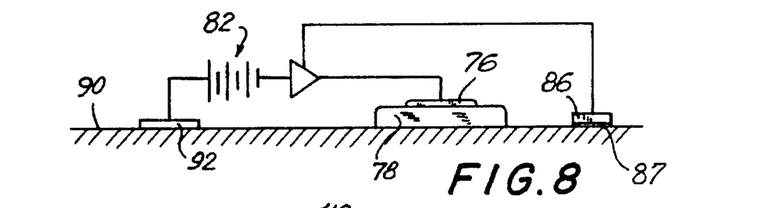
FIG. 8 is an electrical schematic of the circuitry embodying the third or feedback electrode and applicator shown in FIGS. 6 and 7.

In the embodiment of FIGS. 6–8, there is shown an applicator 70 having an outer cover 72 with a raised portion 74 and a lip 75 along the outer periphery. Within the raised portion 74 is a first layer 76, such as a microporous or semi-permeable membrane through which a drug is delivered by means of electrophoretic and/or electro-osmosis activity. As previously noted, in connection with FIGS. 1–2, this first layer may not be needed, depending upon the nature of the medicament and if it is carried by means of a pad or reservoir.

The second layer consists of a flexible reservoir 78 (or pad or other reservoir) containing the drug. The reservoir 78 precludes leakage, but is porous so as to permit drug migrations, be it by means of either or both of said delivery systems noted hereinabove.

The third layer above the reservoir 78 is an extended contact 80 which may be part of one face of the battery 82 which is the next layer. The contact 80 is similar to that of contact 26 described with respect to FIGS. 1–2, and the battery 82 is likewise similar to those previously noted herein.

A further contact 84 above battery 82 is similar to that of contact 80 and same is connected electrically to the opposite side of the battery 82. The cover 72 encloses all layers of the applicator 70 including a third or feedback or sensing device electrode 86 protruding or extending outwardly beyond the rectangular configuration of the applicator 70, and electrically connected to the contact 84 by means of conductor 88.

Insulating material 90 fills the voids between the side of raised portion 74 and the various layers, and also insulates the third or feedback electrode 86 and its wire conductor or lead 88 from coming into contact with any other components of the electrical circuit.

As shown in FIGS. 7–8, contact is made through the skin 90' to the electrically conductive adhesive "electrode" material 92 which coats the underside of lip 75 so that the applicator device 70 is securely adhered in place on the skin 90' with good electrical contact. Such arrangement forms a completed electrical circuit from one side of battery (contact) 82, cover 72, adhesive material 92, skin 90', microporous membrane 76, liquid reservoir 78, and back to battery (contact) 82. The third electrode 86, which feeds back in a loop signal to an amplifier 94, is used as a control probe for sensing drug need. Such electrode or probe is suitably a conventional type which is, for example, ion-responsive and is provided with appropriate enzymes adhered on its surface 87 for sensing a specified chemical in the body or blood so as to regulate same. Such chemical may, for example, be sugar, insulin, or any other component which is desired to be sensed so as to determine the need for a particular drug. Thus, with such a simple feedback loop circuit, the amplified signal generated may be used to achieve a demand type drug delivery system, whereby drug dosage is controllable to a certain extent upon demand. It will be appreciated that the enzymes employed are capable of picking up the concentration of certain chemicals in the body which are desired to be controlled. Upon the enzymes sensing and detecting the particular chemical in the body, a charge or signal generated in the electrode probe is further amplified as required in order to provide a control signal to the applicator battery circuit for regulating the drug dosage to the desired level. Of course, it should be apparent that the electrode incorporates some sort of semi-conductor and/or field effect transistor which receives, amplifies and transmits the signal measured by the probe.

Alternately, the sensing device 86 may be capable of detecting various body parameters that can be sensed, directly or indirectly, at the skin or mucous membrane. Some examples of these body parameters are skin temperature, skin conductivity, pulse rate, capillary dialation, etc.

Figure 9:
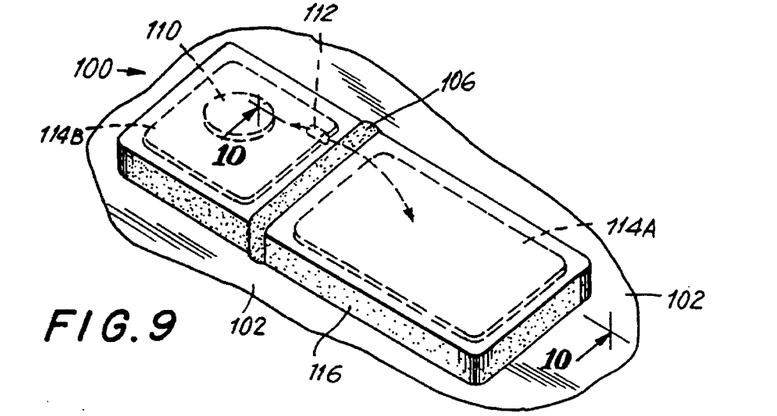
FIG. 9 is a perspective view taken from above or the top of an alternative drug applicator embodying spaced apart electrodes in a side-by-side fashion.
Figure 10:
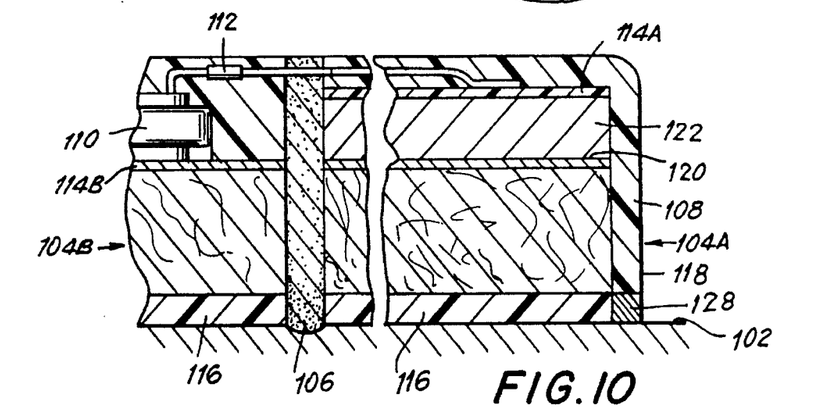
FIG. 10 is a partial cross-sectional view taken along line 10—10 of FIG. 9.

Referring now to FIGS. 9 and 10, a side-by-side patch or drug applicator 100 construction is illustrated affixed to the skin 102. As shown therein, element 104A represents a first electrode and it is spaced apart or separated from a second electrode 104B by a suitable space including an air gap. As best shown in FIG. 6, the gap is suitably illustrated as a "dam" 106 which may be made of an impervious, non-conductive material, such as silicone. Dam 106 maintains electrode separation and provides a seal against the skin so as to preclude any "shorting" effect across the electrodes which might occur due to sweat and other moisture accumulated on the surface of the skin beneath or adjacent to such dam or electrode barrier means. Element 108 is a cover material similar to that outer cover 12 of FIGS. 1–2, although it need not be electrically conductive, since the power source or battery 110 and series connected constant current device 112 (which may suitably comprise a constant current diode) is suitably connected by wire leads or conductors to the separate conductive terminals or film elements 114A and 114B positioned on the first and second electrodes, respectively. Preferred elements may be made of a carbonized plastic foil or other conductive film, such as a metalized mylar.

Membrane 116 positioned along the bottom of both the first and second electrodes is optional as is element 22 of FIGS. 1–4 and comprises a semi-permeable, microporous membrane element having an adhesively and preferably gel-like quality.

Dam 106 is a suitable impermeable, insulating material which is preferably formed so as to protrude beyond membrane 116 and thus form an effective dam-like seal between the separated electrodes forming the applicator device. Thus, dam 106 should be impervious to not only the drugs, water, etc., but it should also be non-conducting.

The second electrode 104B which may also comprise a drug matrix or reservoir is disposed between microporous lower membrane 116 and the conductive element 114B. On the first electrode of the applicator patch 100 there is disposed suitable drug matrix or reservoir 118 such as an electrolyte solution of low concentration between the non-porous membrane 116 and preferably another semi-permeable upper membrane 120 so as to provide for a further (upper) high concentration drug matrix or reservoir 122. Such an arrangement for the first electrode of the patch facilities maintaining a predetermined gradient concentration and desired pH which all aid in providing optimum drug administration.

Figure 11:
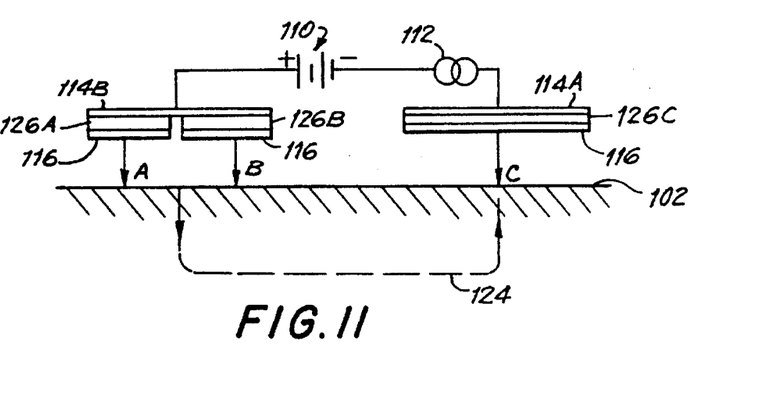
FIG. 11 is a further electrical schematic illustrative of a circuit embodying three active electrodes, such as the active electrode construction exhibited in FIG. 10.

In FIG. 11, which represents an electrical schematic of the invention, numeral 124 indicates current flow shown in phantom generated by the power source or battery 110. Additionally, this figure illustrates schematically an even further applicator construction or modification comprising three distinct electrodes, all of which are "active" electrodes or drug reservoirs, of similar internal construction and they are identified by numerals 126A, 126B and 126C. Reference arrow A emanating from reservoir 126A to skin 102, for example, may be employed to transdermally deliver a drug by means of electro-osmosis, whereas reference arrows B and C emanating from reservoir 126B and 126C, respectively to skin 102 may be employed to deliver transdermally positive ions and negative ions, respectively, by means of iontophoresis or electrophoresis.

The devices of the invention can employ and use some or all electrokinetic phenomena for drug delivery through the skin or mucous membrane, such as electro-osmosis, electrophoresis and iontophoresis. It should also be appreciated that electro-osmosis moves fluid away from the positive to the negative electrode and such mass transfer process is not very dependent upon concentration levels of the drug. On the other hand, iontophoresis takes place at either the positive or negative electrodes and generally requires a low concentration and high dilution as well as a controlled pH.

Accordingly, as noted hereinabove, although FIGS. 9–11 show different electrode constructions, both sides can be of similar construction, and thus both sides would then comprise "active" electrodes in contrast to, as shown, where the left side being an inactive electrode and the right side being an active electrode. With such applicator constructions, it will be appreciated that one or both halves could deliver iontophoretic drugs on one side of the patch and the other patch side could deliver a drug electro-osmotically. Furthermore, electro/chemical parameters may be constructed and arranged so that more than one electro-kinetic phenomena takes place at the same electrode simultaneously or sequentially. As the passage of current to the device induces physical and chemical changes both within the patch and at the skin level, these changes could inhibit or inactivate one electrokinetic mechanism of drug delivery and cause another electrokinetic phenomena to become active. Such a physical or chemical change could be employed to provide a time-dependent, variable rate of drug delivery without changing the current. It could also be employed to sequentially deliver different compounds from within the same reservoir, such as a constrictor and then an antibiotic. It is to be understood that the above-described sequential events could be entirely preprogrammed by a mixture of chemicals loaded in a single drug reservoir.

It should be noted, and as is clearly illustrated in FIG. 9, the electrodes need not necessarily be of the same size (or even shape) although they may be conveniently manufactured to the same size and/or configuration. In a like manner, it will be recognized that these electrodes and applicator constructions in effect do not really incorporate a true "lip" area or skin electrode as does the device of FIGS. 1–4, although a bottom peripheral element 128 still serves as a tacky sealing boundry about the periphery of the applicator, as does element 34 of FIG. 2.

Figures 12, 13:
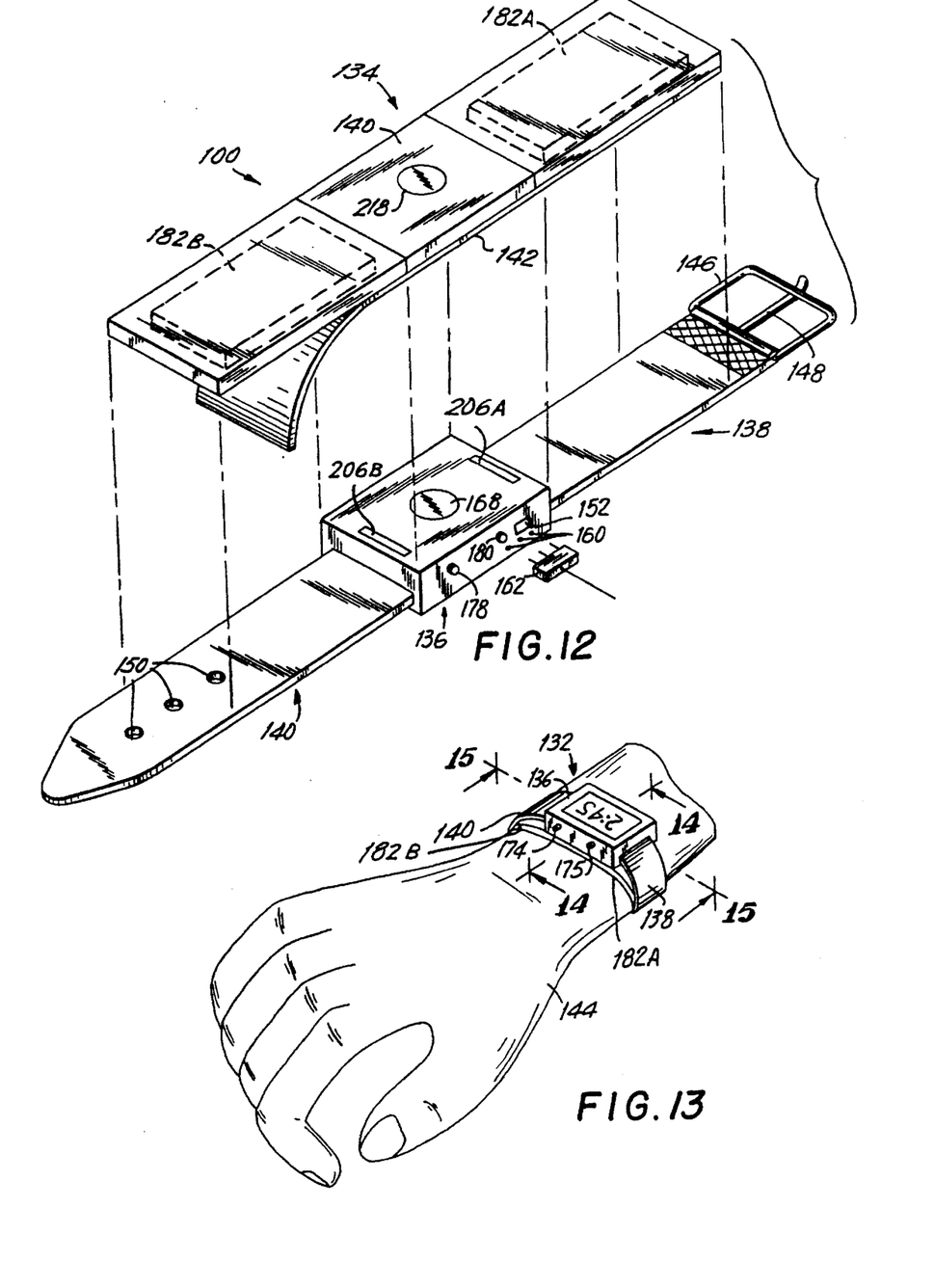
FIG. 12 is an exploded perspective bottom view of a timer and mounting system for a drug applicator.
FIG. 13 is a perspective view of the timer and mounting system shown in FIG. 12 mounted to the wrist of a patient.
Figure 14:
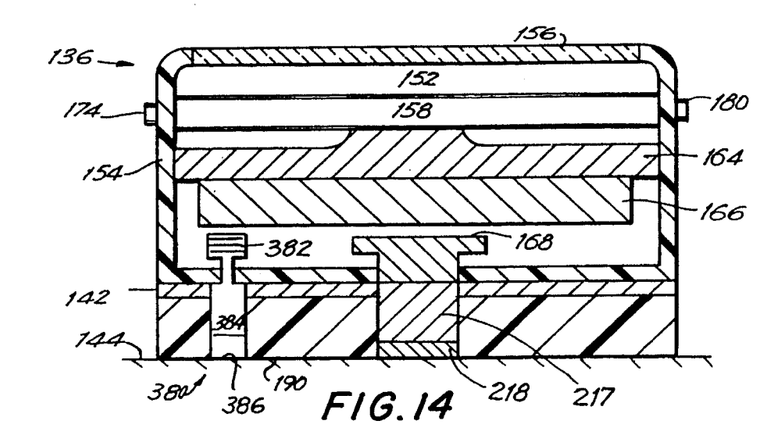
FIG. 14 is a view taken through lines 14—14 of FIG. 13.
Figure 15:
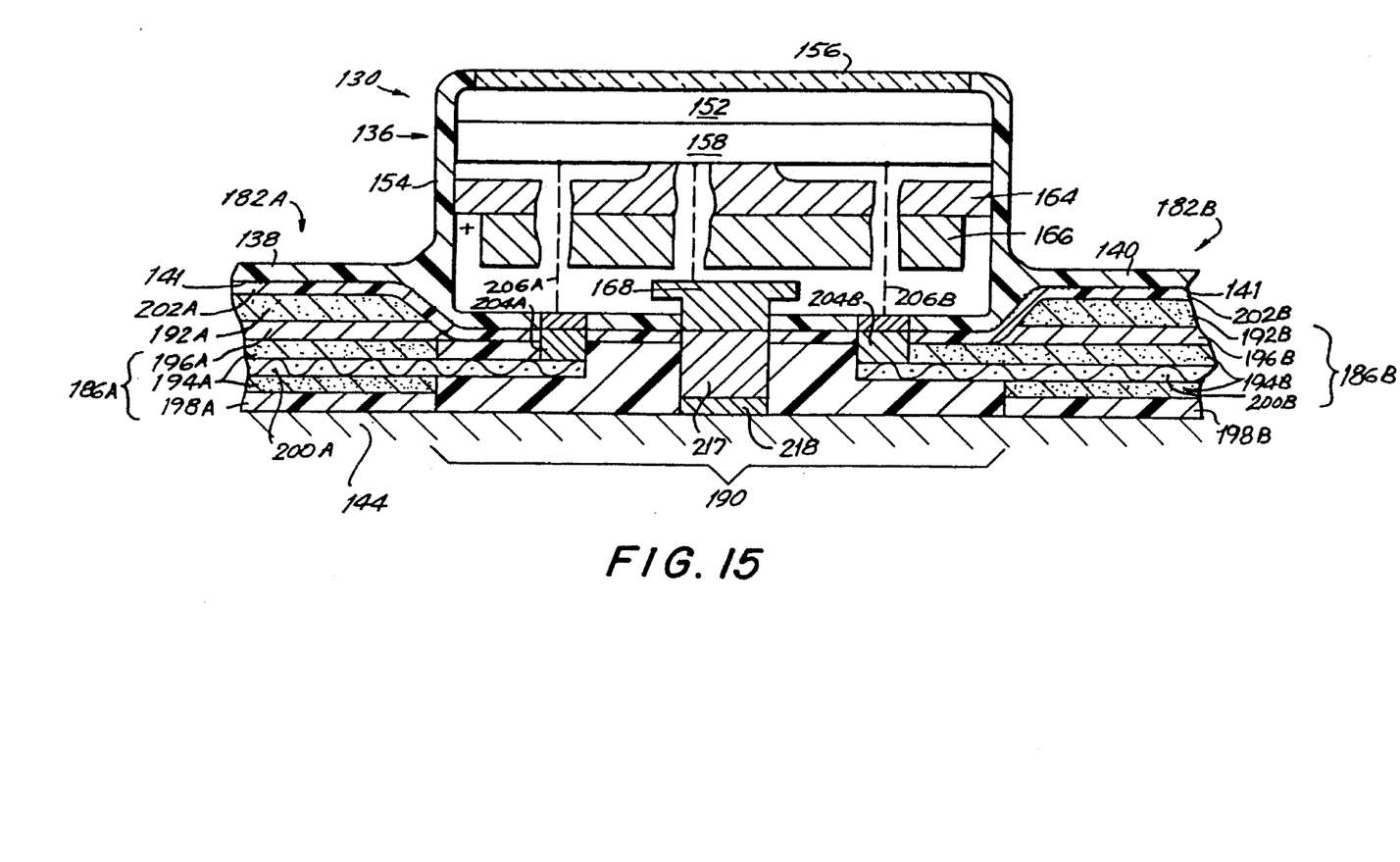
FIG. 15 is a view taken through lines 15—15 of FIG. 14.

The inventive features of the transdermal drug applicator described above are incorporated with a computerized control and mounting system 130 shown in an exploded perspective view in FIG. 12 and in FIG. 13 in a perspective view strapped or braceleted to the body, here shown for purposes of exposition as the wrist 132, of a patient. FIG. 12, which illustrates the invention upside down for purposes of clarification, includes three portions: an elongated drug applicator 134; a watch body 136 containing control and power elements of the system; and a system hold-down strap, specifically a strap buckle portion 138 and strap buckle-on portion 140, each of which is secured to one pair of opposed sides of watch body 136. Applicator 134 is a part of a drug applicator system to be described. The top side of applicator 134 is removably connected to the bottom side of watch body 136 and the bottom side of portions 138 and 140 of the strap by an adhesive layer 141 that is exposed upon removal of a covering backing sheet 142 from the top side of applicator 134. The bottom side of applicator 134 is in close contact with the skin 144 of the patient as shown in FIG. 13. Applicator 134 is configured to the shape of watch body 136 and its strap. As shown in FIG. 12, strap buckle portion 138 has a buckle 146 and a tongue 148 connected to the end of the buckle portion; tongue 148 is adapted to be inserted into one of a series of holes 150 in strap buckle-on portion 140. FIGS. 14 and 15 show a liquified crystal display (LCD) 152 that displays a digital readout of the time.

FIGS. 14 and 15 illustrate interior aspects of watch body 136 and of applicator 134. The interior of watch body 136 will be described first. A watch casing 154 encloses watch body 136, except for a display window 156 positioned at the top of watch body 136 and certain other apertures to be described.

An upwardly facing liquid crystal display (LCD)152 occupies the top layer of watch body 136 directly under window 156 and computer components 158 occupy a layer directly under LCD 152. Computer components 158 include hardware computer components that are adapted to operate special programming instructions associated with the transdermal application of drugs contained in applicator patch 134. Buttons 174 and 176 are mounted to one of the opposed sides of watch body 136 that join the sides to which the strap portions are joined and buttons 178 and 180 are mounted to the opposite side. Buttons 174, 176, 178, 180 are adapted to control the programs contained in computer components 158. FIG. 12 shows a grouping of holes 160 adjoining control buttons 174 and 176 that are adapted to receive the prongs of a plug 162 that in turn is connected to a prepro-gram system (not shown) that is prepared in a doctor's office. Watch battery 164 is positioned in the layer directly below computer component layer 158. An applicator battery 166 is positioned in the layer directly below watch battery 164. Applicator battery 166 supplies the power to operate the drug applicator system to be described associated with applicator patch 134. A feedback electrode 168 (such as feedback or sensor electrode 86 described earlier in relation to FIGS. 6–8) is suitably positioned at the center of watch body 136 directly below applicator battery 166. An aperture formed at the bottom of watch casing 154 gives electrical contact access to applicator battery 166.

As shown in FIG. 15, the drug applicator includes opposed positive and negative applicator patches 182A and 182B, respectively, which perform the function of positive and negative electrodes by being electrically connected in a manner to be described to the positive and negative sides respectively of applicator battery 166 as is shown. As shown pest in FIG. 14, two separate drug pouches 186A and 186B includes strap covering means 138 and 140 at positive and negative patches 182A and 182B respectively of applicator 134. A middle non-conductive neutral portion 190 of applicator 134 separates positive and negative patches 182A and 182B. Positive and negative reservoirs 186A and 186B include upper layers 192A and 192B respectively of a high concentration of a particular drug or drugs and lower layers 194 and 194, respectively of a low concentration of the same drug or drugs. Reservoirs 186A and 186B may each contain a different drug or may each contain the same drug. Also, the drug may be contained in only one of the patches with the opposite patch including a non-drug material acting as an electrode of opposite charge from the drug patch. Upper layers 192A and 192B are separated from lower layers 194A and 194B by semi-permeable membranes 196A and 196B respectively. The lower portions of patches 182A and 182B are micro-porous or semi-permeable membranes 198A and 198B similar to membrane 22 described earlier with reference to FIGS. 1 and 2 through which the drug or medicament migrates to be absorbed through the skin 144.

Flexible, electrically conductive layers 200A and 200B extend between positive and negative reservoirs 186A and 186B respectively and the positive and negative terminals of programmable controller or computer 158. Conductive layers 200A and 200B are preferably positioned generally midway in lower layers 194A and 194B respectively and extend from their generally positive and negative electrode positions respectively from reservoirs 186A and 186B into neutral or middle portion 190. Highly conductive connectors 204A and 204B in neutral portion 190 connect the inner ends of mesh layers 200A and 200B, respectively, to the positive and negative terminals of programmable computer 158 by way of conductors 206A and 206B respectively embedded in the top of watch casing 154.

The applicator system can include a negative ion drug in negative reservoir 186B and either a positive ion drug or a neutral drug operating by way of electro-osmosis in positive patch 186A. Conductive layers 200A and 200B are preferably made of electrically conductive carbon fibers that are woven together with conductive, hair-like protrusions emanating from the weave. Alternately, flexible layers 200A and 200B are made of flexible electrically conductive strands loaded with electrically conductive carbon particles. An electrical circuit between applicator battery 166, programmable computer 158, conductive mesh layer 200A, membrane 196A, reservoir 186A, skin 144 of the patient, membrane 196B, reservoir 182B, conductive mesh layer 200B, connector 204B, conductor 206B, computer 158, and then to the other terminal of applicator battery 166 is thus created. The connections between the batteries 164 and L66 and the computer 158 are not shown for simplicity of illustration. When the negative side reservoir 186B is supplied with a drug ionized negatively, the drug will be repelled from the negative side charge into skin 144 of the patient by iontophoretic activity.

When positive side patch 186A is supplied with a drug ionized positively, the drug will be repelled from the positive side through the skin 144 of the patient by iontophoretic activity. Alternatively, positive side reservoir 186A can be supplied with a drug of neutral charge so that the drug will be moved into skin 144 of the patient by electro-osmotic activity.

Impermeable sealing layers 202A and 202B extend across the tops and outer sides and edges (not shown in FIG. 15) of patches 182A and 182B respectively so as to partially enclose high concentration reservoirs drug 192A and 192B, respectively. Layers 202A and 202B are joined to non-conductive middle portion 190 and to semi-permeable bottom membranes 198A and 198B respectively so that drug reservoirs 186A and 186B are completely enclosed. Adhesive layer 141 is secured to the top side of sealing layers 202A and 202B and of non-conductive neutral portion 190 by an adhesive material (not shown) and is further secured to the underside of strap cover portions 138 and 140 and of watch casing 154. Watch body 136 and strap portions 138 and 140 are demountable from applicator 134 so that watch body 136 can be reused.

Figure 16:
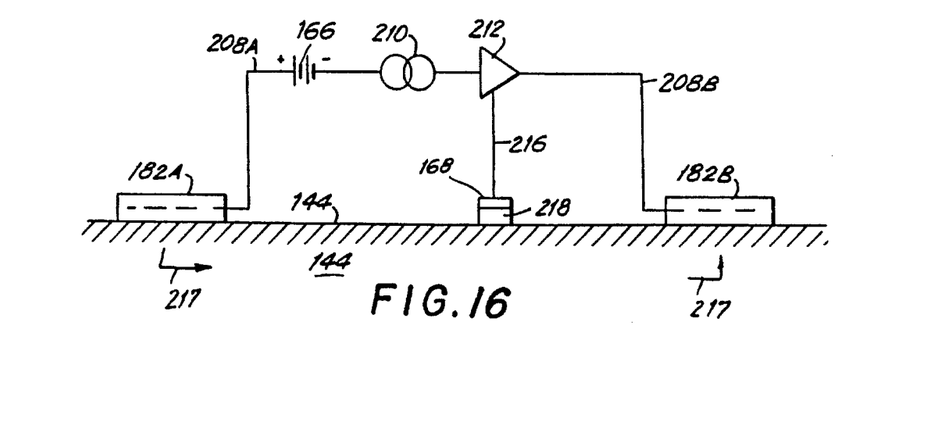
FIG. 16 is a schematic electric circuitry of the embodiment shown in FIGS. 12–15.

Third, or feedback sensor 168 is in electrical contact with the programmable computer 158 as shown best schematically in FIG. 15. As seen in FIG. 16, leads 208A and 208B electrically connect positive side patch 182A and negative side patch 182B with the positive and negative sides respectively of battery 166 and programmable computer 158 (illustrated in FIG. 16 as current regulator 210 and programmer 212). A lead 216 connects third feedback sensor 68 with programmable computer 212. Current 217 from the power source or battery 166 moves through lead 208A, drug reservoir 182A, skin 144, drug reservoir 182B, lead 208B, programmable controller 212, current regulator 210, and returns to battery 166. The sensor 168 includes a skin control portion 218. The contact layer 218 may be, for example, a pH sensor or an ion-sensitive electrode that senses skin changes in the patient. Layer 218 is capable of sensing chemical or physical changes in the surface of skin 144 with the capability of passing the senses changes to third electrode 168 which in turn feeds back a loop signal via lead 216 to programmable computer or controller 212. Sensing drug need and signalling such need to controller 212 is primary function of feedback sensor 168. Sensor 168 may be preferably ion responsive and layer 218 can be provided with appropriate enzymes for sensing a specified chemical to be regulated in the body or blood. Sugar and insulin are examples of typical chemicals to be regulated.

Figure 17:
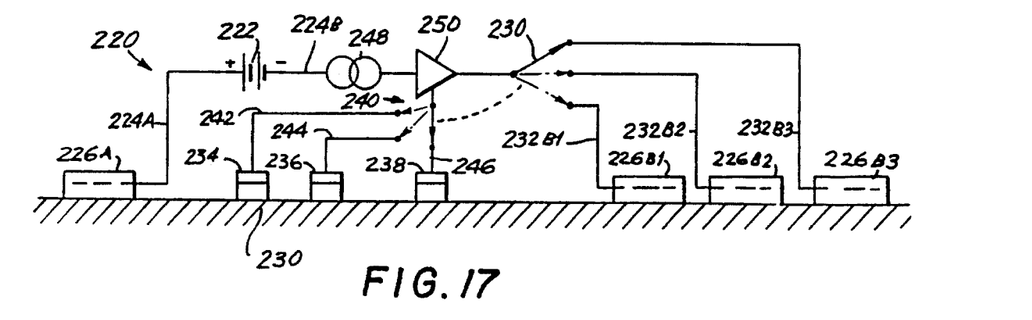
FIG. 17 is a schematic electric circuitry for a multi-drug applicator delivery system similar to the embodiments shown in FIGS. 12–16.

FIG. 17 is an electrical diagram representation of an alternate embodiment to the system shown in FIGS. 12–16. As shown in FIG. 17, an applicator system 220 is mounted with straps and a computerized watch body similar to cover straps means 138 and 140 and watch body 136 described above in relation to applicator system 130. System 220 includes an applicator battery 222 having a positive lead 224A to positive side drug reservoir 226A positioned in a positive side patch similar to patch 182A described earlier with reference to FIG. 16. Patch 226A is in contact with skin 230 of a patient. System 220 further includes a negative side lead 224B to three negative side reservoirs 226B1, 226B2, and 226B3 in parallel relationship to one another positioned in a negative side patch similar to patch 182B described earlier with reference to FIG. 16 except that three separate reservoirs are positioned in the patch rather than one. Each reservoir 226A, 226B1, 26B2 and 226B3 is capable of containing a separate drug in accordance with the medical needs of the patient. A drug reservoir selector switch 230 is capable of being controlled by a self-contained programmable computer microprocessor to a selected electrical path, from lead 224B to one of the leads 232B1, 232B2, or 232B3 to drug reservoirs 226B1, 226B2 or 226B3, respectively as preprogrammed either by an external programmer via plug 162 (FIG. 12) or by the pre-coded disposable drug reservoir shown in FIG. 21 via electrical conductive paths or switch activating elements 369 and/or 371.

Switch 230 can be controlled by programmed input from the computer mechanism in the watch body in accordance with body needs as monitored by three separate feedback sensors 234, 236 and 238 each similar to feedback sensor 168 described previously positioned in the neutral portion of the system similar to neutral portion 190 of applicator system 130. Sensors 234, 236 and 238 are sensitive to skin changes relative to the drugs in reservoirs 226B1, 226B2, and 226B3, respectively. A feedback sensor selector switch 240 is positioned in the watch body of system 220 and is part of the programmable computer, or controller, 250. Switch 230 is controlled by the same programmable computer microprocessor so as to select an electrical path from lead 224B to one of the leads 242, 244 or 246 to feedback sensors 234, 236 or 238, respectively. Selector switch 240 is preferably automatically switched to the proper path for the feedback electrode sensor upon energization of selector switch 230 to activate the selected drug reservoir. A programmable current control source represented by 248 and controller 250 are placed in series on lead 224B of applicator battery 222.

Figure 18:
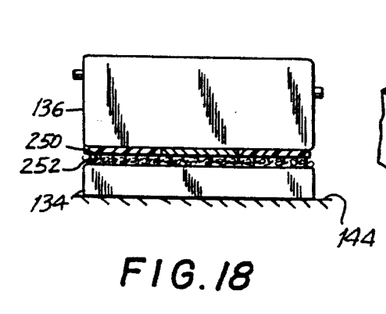
FIG. 18 is an isolated side view of a watch and applicator joined by a snag-and-hook connector.

FIG. 18 illustrates a connector between watch body 136 and cover strap portions 138 and 140 and applicator 134 shown in FIGS. 12–15 as an alternative to adhesive layer 141 exposed upon removal of backing sheet 142. Here the bottom of watch body 136 and of strap portions 138 and 140 (not shown) are provided with one layer 250 of a snag-and-hook connector and the top of applicator 134 is provided with the other layer 252 of the snag-and-hook connector. Such connection means may comprise alternatively any conventional fasteners, such as buttons, snap-on devices, a magnet, and the like. Preferably, fasteners of the "Velcro" type are convenient (a trademark of the Velcro Corporation of America).

Figure 19:
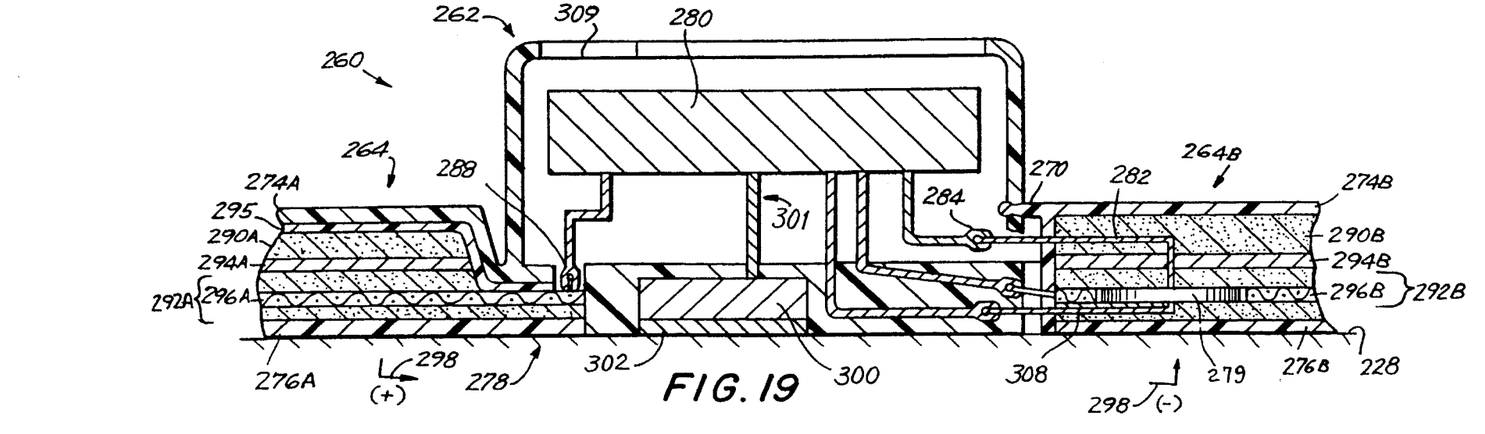
FIG. 19 is a cross-sectional view of a watch/computer incorporated with one strap and one removable strap containing an applicator battery.

FIG. 19 illustrates two embodiments of the invention. In one embodiment (shown on the left side of the watch body 262) an applicator system 260 includes a watch body 262 and a first strap-and-patch combination 264A unitary with the watch casing of watch body 262; and a second embodiment (shown on the right) illustrate strap-and-patch combination 264B that is removably attached to watch body 262 by upper snap-on connector 270. In either embodiment, strap combinations 264A and 264B are enclosed at their top sides by flexible impermeable covers 274A and 274B and on their bottoms by permeable lower membranes 276A and 276B which are in contact with the skin 278 of the patient. Flexible covers 274A and 274B are adapted to function as straps. In the combination 264B embodiment, an applicator battery 279 is positioned in replaceable patch 264B with an insulated electrical lead 282 from the positive side of the battery 279 to a connector 284 removable positioned in watch body 262 in electrical connection to an internal lead. Electrical receptacle 284 is internally connected to the programmable computer 280 which is mounted in watch body 262. Optionally, another battery (not shown) may be provided in the watch case for the purpose of maintaining power to a computer 280, which preferably includes a computer battery that maintains computer memory and data during downtime when the applicator is being reloaded or not in use while combination 264 is being replaced. This same battery can be used to provide the required power for the combination 264A embodiment which can be made either with or without a self-contained battery in the applicator itself.

Upper reservoirs 290A and 290B containing concentrated drug or drugs and lower reservoirs 292A and 292B containing a diluted drug or drugs are positioned in patch combinations 264A and 264B respectively. Semipermeable membranes 294A and 294B separate upper and lower reservoirs 290A and 290B and upper and lower reservoirs 292A and 292B, respectively. Elongated flexible, electrically conductive layers 296A and 296B are positioned in patch combinations 264A and 264B respectively in the mid-portions of lower reservoirs 292A and 292B. Conductive layers 296A and 296B are preferably similar in construction and arrangement to mesh layers 200A and 200B described earlier. Patch combination 264A may be positively charged with current passing through lower membrane 276A through skin 278 to negatively charged patch 264B through lower membrane 276B so that patch combination 264B is negatively charged. Current 298 is indicated by arrowed lines. Patch combinations 264A and 264B act as positive and negative electrodes for the system.

A third feedback sensor 300 is positioned in watch body 262 with a contact layer 302 in contact with skin 278 so that skin chemical parameters are transmitted to computer 280 by way of a lead 301 in watch body 262. Feedback sensor 300 is analogous to feedback sensor 168 and includes controller (not shown) similar to controller 212 shown in FIG. 16.

Second strap/patch 264B along with applicator battery 279 is noted to be replaceable or disposable, while first strap/patch 264A with watch body 262 can be replenished by another drug reservoir adhesively attached to the strap 274A. First strap/patch 264A can of course be made without a reservoir portion with a simple positive electrode to complete the circuit generated by applicator battery 280. Watch body 262 as shown in FIG. 19 includes features analogous to the watch body 136 shown in FIGS. 12–15 except for the placement of applicator battery 279 in the replaceable patch embodiment 264B. Watch body 262 also includes LCD 309.

All electrical components in FIG. 19 are connected to the centrally disposed computer 280 by suitable conductors similar to 284 or 288 (as in the strap combination 264A). Also, in the replaceable drug reservoir and electrode of the 264A embodiment, the "patch" is provided with a suitable adhesive coating (not shown) between the strap 274A and the impermeable covering means 295.

Figure 20:
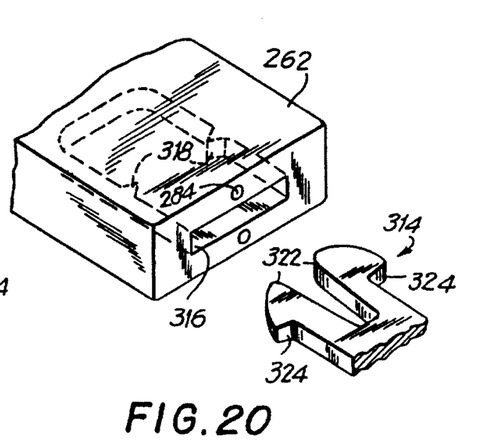
FIG. 20 is a schematic cross-sectional view of a watch/computer incorporating a single refillable drug applicator reservoir.

FIG. 20 shows an alternate connector device to the snap-on connectors described for FIG. 19 for removably securing the disposable strap/patch 264B to watch body 262. A single flat mounting element 314 connected to the inner side of strap/patch 364B (not shown) is adapted to be biasingly slid into a flat recess 316 formed at the side of watch body 262. Opposed protrusions 318 are positioned in recess 316 engage biasedable ends 322 at notches 324 for latching so that strap/patch 264B is removably secured to watch body 262. Mounting element 314 can be removed from recess 316 by pulling element 314 from the recess while at the same time laterally squeezing 314 with enough force to overcome the spring force or biasing action of the connector. The recess 284 is for the connecting lead 282 and other like recesses are provided for the other electrical connections.

Figure 21:
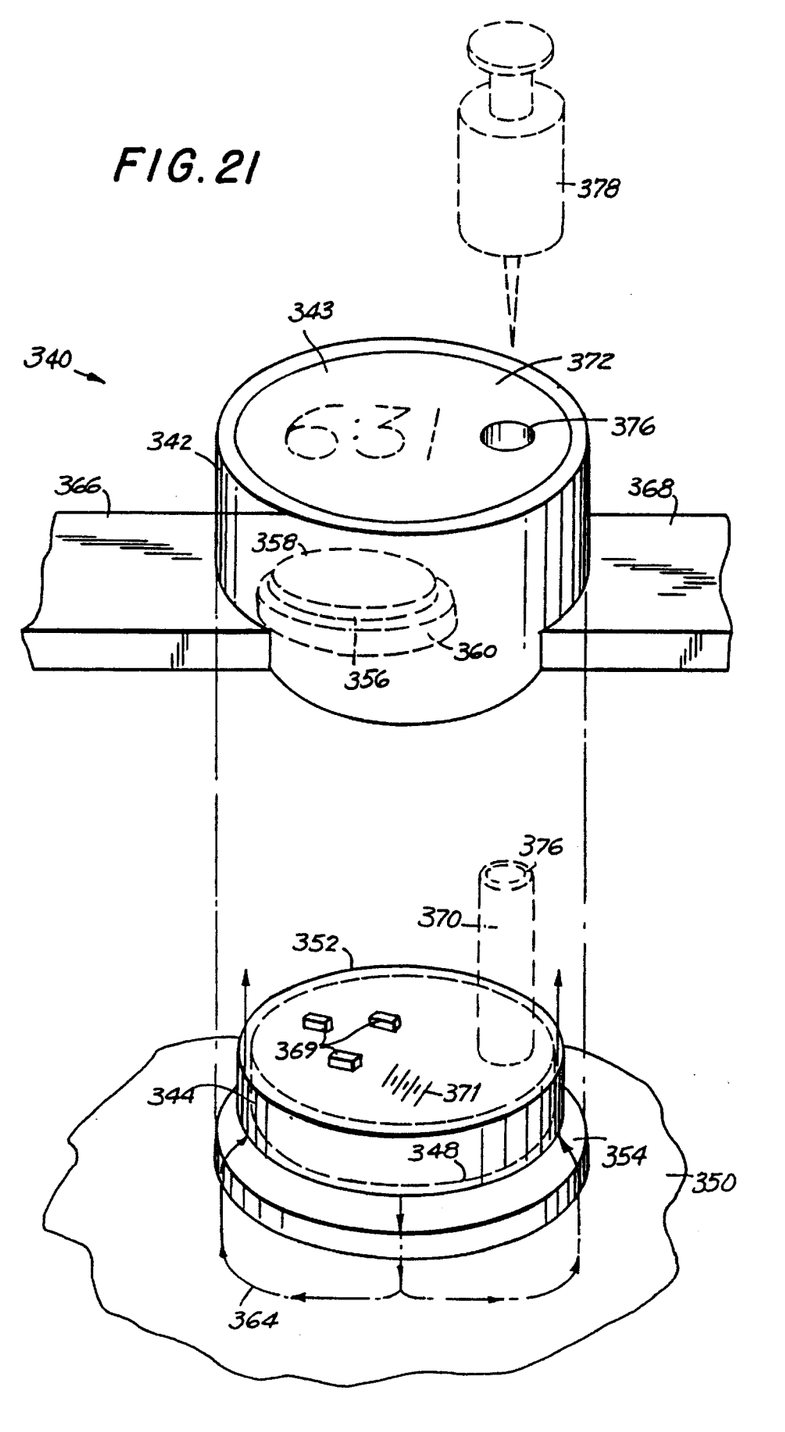
FIG. 21 is a perspective view of a watch body with a replaceable applicator with an alternative refillable reservoir shown in phantom.

FIG. 21 illustrates an embodiment of the invention wherein a replenishable applicator or patch is positioned in the watch body. The reservoir of the patch is either refillable or can be part of a throwaway cartridge that can be positioned in the watch body.

Applicator system 340 includes a watch body 342 with an LCD 343, a computer assembly and a computer battery (neither shown) that are analogous in operation to the computer 158 and computer battery 166 described in relation to the embodiment shown in FIG. 15. Watch body 342 is shown for purposes of exposition as cylindrical but it could also be of any other shape, such as square or rectangular as shown for the embodiments described earlier. The drug reservoir 344 includes a microporous membrane 348 which is in contact with the skin 350 of the patient. The medicament contained in the reservoir 344 is delivered through skin 350 of the patient as previously explained herein. Reservoir 344 can be made in various forms generally analogous to those embodiments of FIGS. 1–11. Reservoir 344 includes cover 352 and an outwardly extending circular lower lip or conductive flange portion 354 that contacts the skin 350. An applicator battery 356 is positioned in watch body 342 over the reservoir 344. Applicator battery 356 has opposed top and bottom electrical contact layers 358 and 360 respectively. A conductive adhesive layer (not shown) such as adhesive material 36 of FIG. 1 under the outer lip or rim of flange portion 354 is provided to allow the movement of electrical current indicated by phantom lines 364 from the semi-permeable drug reservoir membrane 348, skin 350, and flange 354. Of course, in this embodiment of the invention, a programmable computer (not shown) and current conditioning means are employed in a similar manner to control drug delivery as is described herein with respect to FIG. 15.

As shown in FIG. 21, the "hat-shaped" assembly can be removed in the manner of a cartridge from the bottom of watch body 342 with flange portion 354 being the bottom wall of watch body 342 when installed in operative relationship in the watch body. Electrical current 364 flows upon placement of membrane 348 against skin 350. The cartridge may be suitably secured to the watch body by various means, such as detents at the periphery of flange portion 354 or by snap-on type connectors. Straps 366 and 368 can be unitary with watch body 342 as shown or can be separately mounted to the watch body. Switch activating cams 369 extending upwardly from the face of the top wall of reservoir 344 are adapted to mate with a plurality of recesses in the watch body so that programmed responses will be activated within the programmable computer. The position of the switch activating cams 369 is predetermined in accordance with the type of drug medicament contained in reservoir 344. Alternatively, a conductive bar code 371 suitably provided on the top face of reservoir 344 may be employed to activate programmed responses in accordance with the drug contained in the reservoir.

An alternate embodiment for replenishing the drug from the reservoir includes an elongated filling tube 370 as shown in phantom lines in FIG. 21. Top face 372 includes an LCD 343. Filling tube 370 includes a self-sealing top cover 376 made of rubber or similar material that can be penetrated by the needle of a syringe 378 shown in phantom lines that contains a refill of the depleted drug in reservoir 344.

An example of one type of monitoring device that can be combined with the programmable computer contained in a watch body may be a heart-monitoring device 380, as shown in FIGS. 14. Such devices are well-known and conventional in that, for example, a jogger's watch may employ a LED and a photo-transistor to determine the heart rate (pulse) or a thermister to measure skin temperature. As shown in FIG. 14, the light emitting diode (LED) 382 is positioned in watch body 136 over a vertical light tube 384 formed in neutral portion 190 of applicator 100. The bottom aperture 386 of tube is in direct contact with the skin 144 of a patient so that the light reflected from the skin is measured by a photocell (not shown) and the variations of the reflected light are used to compute the pulse rate.

A buffering agent maintains the pH level in a solution or mixture within a range of values by neutralization of acid in the system. The rate of absorption of a drug is dependent on the pH level; if the system becomes completely acidic, the drug will not be absorbed. In addition, when a current is passed through an interface such as at an electrode and the skin, an electrolyte breaks down into an acid and a base at the interface. Current alone can change pH but the effect can either help the rate of absorption or hinder the rate. Therefore, a buffering agent in the drug reservoir or at the skin interface is desirable for the practical functioning of the drug absorption systems being discussed here. It is noted that two or more buffering agents in the system may be required so that when one agent is exhausted another agent can begin to activate.

With an electrokinetic transdermal drug applicator of the invention, having drug reservoirs with at least one drug and a plurality of electrodes with a power source for providing the mass transfer of the drug through the skin by electrokinetic phenomena, it is the well known buffering means associated with the drug reservoir and the skin interface which is capable of maintaining a pH for an optimum drug delivery rate. Moreover, upon exhaustion of a predetermined amount of the buffering means caused by electrical current flow, the pH environment in the drug reservoirs and at the skin interface changes which in turn changes the rate at which a drug is delivered. It will be appreciated that such a change may be one of either increasing or decreasing the rate of drug delivery, or one of termination.

In addition, with additional drugs and other conventional buffering agents or means in the reservoirs, such additional buffers become active upon predetermined pHs in the reservoir upon exhaustion of first, second, etc. buffers in a sequential manner. Thus, each of the buffering means is adapted to activate or deactivate over a specific range of the pH in the drug reservoirs. In another modification of the invention, a pH indicating dye is provided in the applicator which dye is capable of displaying various colors at various pH levels within the applicator. With a transparent cover (61 in FIG. 5) or a suitable window (like 50 in FIG. 1) in the applicator, the colors are visible therethrough sequentially indicating the activity of the applicator and which drug is being delivered at any one time through the skin as well as the time for removal of the drug applicator from the skin. In this regard, appropriate color reference zones along a peripheral (immediate vicinity about suitable window as can be provided) area or edge of such a window for comparing the color change of the indicator dye to the color reference zones to signal at least the remaining time before need for removal and which drug is being administered at such moment in time. Of course, the window need not be round as shown therein, but may be of any shape, such as rectangular, oval, square, and the like. Such zones are like a color bar chart.

Another advantage of buffering agents is that they maintain the pH range of the skin at the interface by limiting the pH changes taking place at the skin interface to reside within a predetermined range which is non-irritating to one's skin.

It should also be noted that the mounting means may take the form of any suitable arrangement including, but not limited to the following structures: head band, arm or leg band, wrist bracelet or watch strap, body belt, and the like. As the applicator is made disposed between the mounting means and the skin or mucous membrane, other arrangements include tampon-like inserts or other like devices for use in the vaginal canal or other body cavities. With such structures, the applicator means may be removably or permanently mounted to a core-like element (which may contain some of the elements of the apparatus) and the applicator means itself would in effect be disposed or wrapped about the core.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A two-part replenishable drug applicator system for transdermal drug delivery of at least one drug to the systemic blood of a human being or animal through skin thereof comprising:

a reusable assembly having a computer control part of said drug applicator system removably mountable on said human or animal for control of transdermal delivery of at least one drug through the skin;

said computer control part including a source of electrical energy for electrically energizing said drug applicator system and effecting flow of current through the skin;

a drug containing cartridge comprising a replaceable drug reservoir for containing at least one drug and replaceably mountable on said computer control part in a separable assembly for replenishing said drug applicator system with at least one drug as required;

said drug reservoir having a permeable surface for contacting the skin of said human being or animal when said drug reservoir is mounted on said computer control part; and means on said drug reservoir and means on said computer control part for cooperative association when said drug reservoir is mounted on said computer control part effectively establishing a current flow path from said computer control part to said drug reservoir and through the skin of said human being or animal for application of controlled electrical current to said drug reservoir for application of a drug through said surface thereof in contact with the skin of staid human being or animal.

2. A two-part replenishable drug applicator system according to claim 1, in which said computer control part comprises a watch body.

3. A two-part replenishable drug applicator system according to claim 1, in which said computer control part comprises a programmable computer.

4. A two-part replenishable drug applicator system according to claim 1, in which drug reservoir comprises a permeable membrane defining said surface.

5. A two-part drug applicator system according to claim 1, in which the means on said computer control part and the means on said drug reservoir comprise switch means for cooperative associate in establishing automatically said current flow path.

6. A two-part drug applicator system according to claim 1, in which said drug reservoir comprises a filling tube, and said computer control part having a bore for access to said tube extending therethrough, the tube having a puncturable self-sealing seal at an exterior end thereof for introduction of a replenishment drug into said drug reservoir with a syringe for penetrating said puncturable self-sealing seal and enabling said replenishment drug to be forced into said drug reservoir.

7. A two-part replenishable drug applicator system according to claim 1, in which said reusable assembly and said cartridge are coupled together and said cartridge underlies said computer control part of said reusable assembly when coupled thereto.

* * * * *